(12) United States Patent
Winters

(10) Patent No.: US 6,881,958 B2
(45) Date of Patent: Apr. 19, 2005

(54) PHOSPHOR PLATE POSITIONING DEVICE

(75) Inventor: William P. Winters, New Rochelle, NY (US)

(73) Assignee: Flow X-Ray Corporation, West Hempstead, NY (US)

( * ) Notice: Subject to any disclaimer, the term of this patent is extended or adjusted under 35 U.S.C. 154(b) by 139 days.

(21) Appl. No.: 10/241,933

(22) Filed: Sep. 11, 2002

(65) Prior Publication Data

US 2004/0046133 A1 Mar. 11, 2004

(51) Int. Cl.[7] .................................................. A61B 6/14
(52) U.S. Cl. ....................... 250/353; 378/191; 378/169; 378/168
(58) Field of Search .......................... 250/583; 378/191, 378/169, 168

(56) References Cited

U.S. PATENT DOCUMENTS

| | | | | |
|---|---|---|---|---|
| 4,082,957 A | * | 4/1978 | Morlan ........................ | 378/156 |
| 4,625,325 A | * | 11/1986 | Beraudo ...................... | 378/168 |
| 5,025,465 A | * | 6/1991 | Bauer et al. ................. | 378/169 |
| 5,128,978 A | * | 7/1992 | Roth et al. ................... | 378/185 |
| 5,265,865 A | * | 11/1993 | Agano et al. ................. | 271/1 |
| 5,454,022 A | * | 9/1995 | Lee et al. ..................... | 378/98.8 |
| 5,475,230 A | * | 12/1995 | Stumpf et al. ............. | 250/484.4 |
| 6,042,267 A | * | 3/2000 | Muraki et al. .............. | 378/169 |
| 6,315,444 B1 | * | 11/2001 | Koren ......................... | 378/169 |
| 6,382,831 B1 | * | 5/2002 | Bacchetta et al. .......... | 378/170 |
| 6,398,409 B1 | * | 6/2002 | Brooks ........................ | 378/209 |
| 6,520,676 B1 | * | 2/2003 | Schmitz ....................... | 378/191 |
| 2002/0076002 A1 | * | 6/2002 | Eppinger et al. ........... | 378/170 |
| 2003/0047696 A1 | * | 3/2003 | Brahm et al. ............... | 250/584 |
| 2003/0066973 A1 | * | 4/2003 | Misawa et al. ........... | 250/484.4 |
| 2003/0112921 A1 | * | 6/2003 | Lang et al. ................... | 378/54 |
| 2004/0170253 A1 | * | 9/2004 | Landis et al. ............... | 378/168 |
| 2004/0188625 A1 | * | 9/2004 | Schulze-Ganzlin .... | 250/370.09 |

OTHER PUBLICATIONS

CRA–Clinical Research Associates Newsletter—vol. 23, Issue 9,3 pages, Sep. 1999.
Air Techniques Inc. "Getting Accurate Digital Images Shouldn't Be Hard Work". 1 page. 2003.
Air Technique Inc. "ScanX" Vacuum Systems, Digital Imaging System. 3 pages. Accessed on Internet Aug. 22, 2003.
"Basics of Charge–Coupled Devices" Keith Wetzel, Eastman Kodak Co. Medical Design News, 2 pages. Nov. 2003.
Pneutronics General Valve, "Pneutronics Puts Repeatable Precision Control..." Medical Design News. 1 page. Date unknown.

* cited by examiner

Primary Examiner—David Porta
Assistant Examiner—Christine Sung
(74) Attorney, Agent, or Firm—John L. Rogitz

(57) ABSTRACT

A phosphor plate positioning device includes a rigid magazine having a back plate and a door hingedly attached to the back plate. The back plate forms a cavity that is sized and shaped to receive a phosphor plate and a support arm can be engaged with the magazine in order to properly position the magazine and phosphor plate within a patient's mouth relative to a dental x-ray cone.

18 Claims, 3 Drawing Sheets

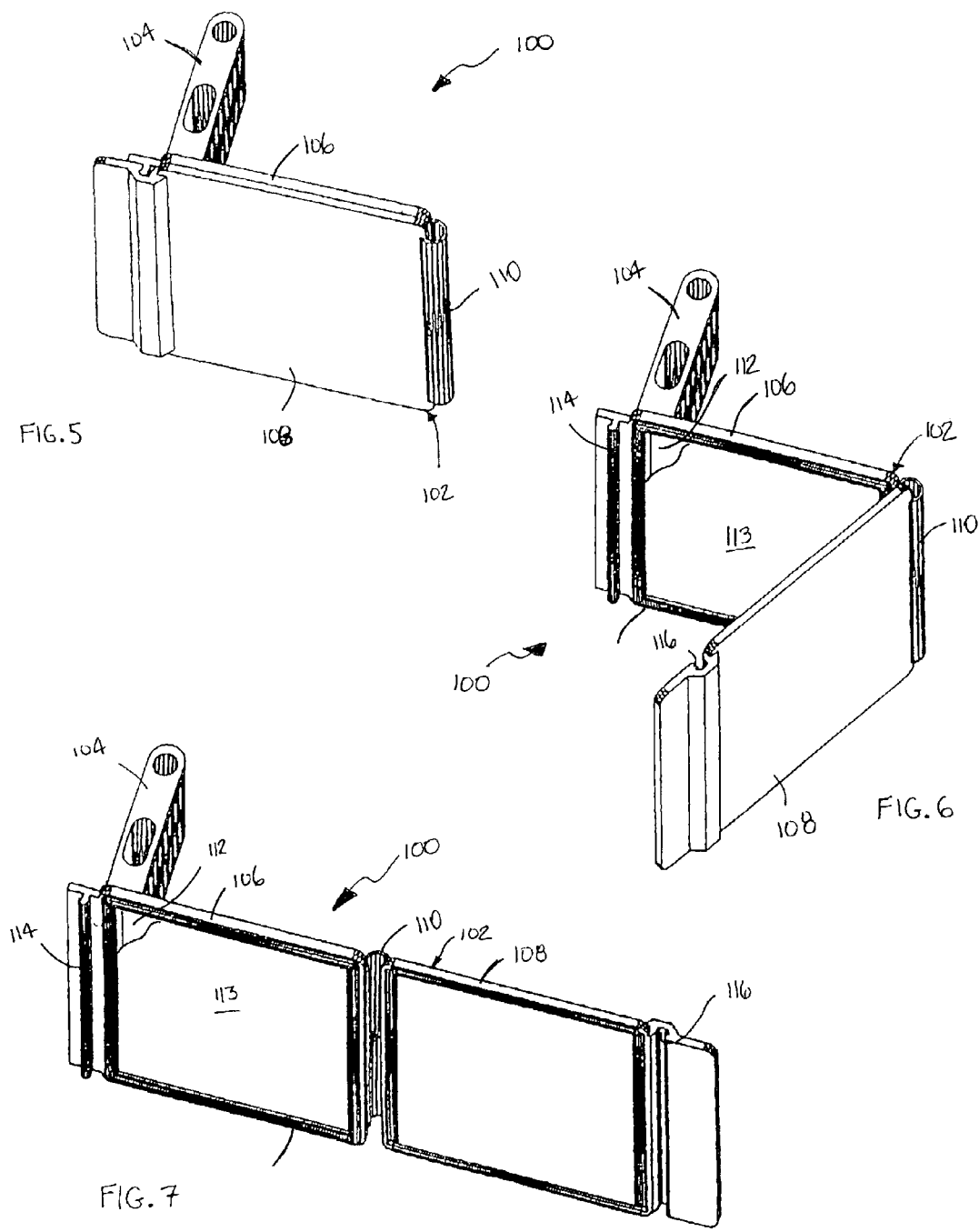

PHOSPHOR PLATE POSITIONING DEVICE

FIELD OF THE INVENTION

The present invention relates to dental imaging plates.

BACKGROUND OF THE INVENTION

Dental x-rays are extremely valuable tools that can be used by dentists to examine and diagnose patients' teeth and gums. By using dental x-rays, a dentist can view tooth and gum anatomy that is otherwise invisible to the naked eye. Dental x-rays can also be used to inform and educate patients regarding the health of their teeth, gums, and other related oral anatomy.

Conventional dental x-rays are taken using relatively small films for obtaining views of one or two teeth or for obtaining panoramic views of a patient's teeth and gums. These films are exposed using a dental x-ray machine; processed using specialty developer, fixer solutions, and equipment; and viewed on a light box in their original size and shape.

A relatively new type of dental imaging includes the use of thin, rigid phosphor plates in place of traditional dental x-ray film. These phosphor plates are approximately the same size as conventional dental x-ray film and can be exposed via a dental x-ray machine. The phosphor plates can then be placed inside a special scanner that reads the image off the plate and transmits the image to a computer for diagnosis, manipulation, and storage. The plates can them be erased and re-used.

Unlike conventional dental x-ray film, the phosphor plates must remain unbent at all times. In other words, if the plates are bent or creased, they are permanently damaged and cannot effectively be used to capture images. Phosphor plates must also be handled very carefully—preferably by the edges and they must be used in a moisture free environment. Also, the imaging side of a phosphor plate cannot be exposed to light for more than two seconds without affecting the quality of the image recorded.

Presently, flaccid vinyl wrappers are provided for handling phosphor plates. A phosphor plate can be placed inside a vinyl wrapper with the imaging side of the plate adjacent to an opaque side of the wrapper. Accordingly, the wrapper can protect the phosphor plate from moisture and light. Unfortunately, the flaccid vinyl wrappers do not prevent damage to the phosphor plates from bending or creasing. Moreover, the vinyl wrappers do not aid dental professionals in positioning the plates in relation to patients' teeth for accurate imaging.

The present invention has recognized these prior art drawbacks, and has provided the below-disclosed solutions to one or more of the prior art deficiencies.

SUMMARY OF THE INVENTION

A phosphor plate positioning device includes a rigid magazine. A cavity is formed within the magazine and is sized and shaped to receive a phosphor plate. Preferably, the magazine includes a back plate that forms the cavity and a door that is hingedly attached to the back plate. In a preferred embodiment, a support arm is engaged with the magazine. The support arm can be integrally formed with the back plate. Preferably, a seal circumscribes the cavity. Moreover, the support arm is formed with one or more bores and a portion of the support arm is knurled. In a preferred embodiment, the back plate includes a rib adjacent to the cavity. Also, the door includes a groove that is configured to engage the rib in order to keep the door closed.

In another aspect of the present invention, a dental imaging system includes a phosphor plate and a non-flaccid magazine that is sized to hold the plate. The magazine is partially opaque in order to prevent an imaging surface of the phosphor plate from being exposed to light when the plate is held in the magazine.

In yet another aspect of the present invention, a method of dental imaging includes providing a rigid magazine. A phosphor plate is placed within the magazine. Then, the rigid magazine and phosphor plate are placed adjacent to one or more teeth and the phosphor plate is exposed to x-rays.

BRIEF DESCRIPTION OF THE DRAWINGS

The present invention will now be described, by way of example, with reference to the accompanying drawings, in which:

FIG. 5 is a perspective view an alternative phosphor plate positioning device;

FIG. 6 is a second perspective view of the alternative phosphor plate positioning device; and FIG. 7 is a third perspective view of the alternative phosphor plate positioning device.

DESCRIPTION OF THE PREFERRED EMBODIMENT

Figure 1:
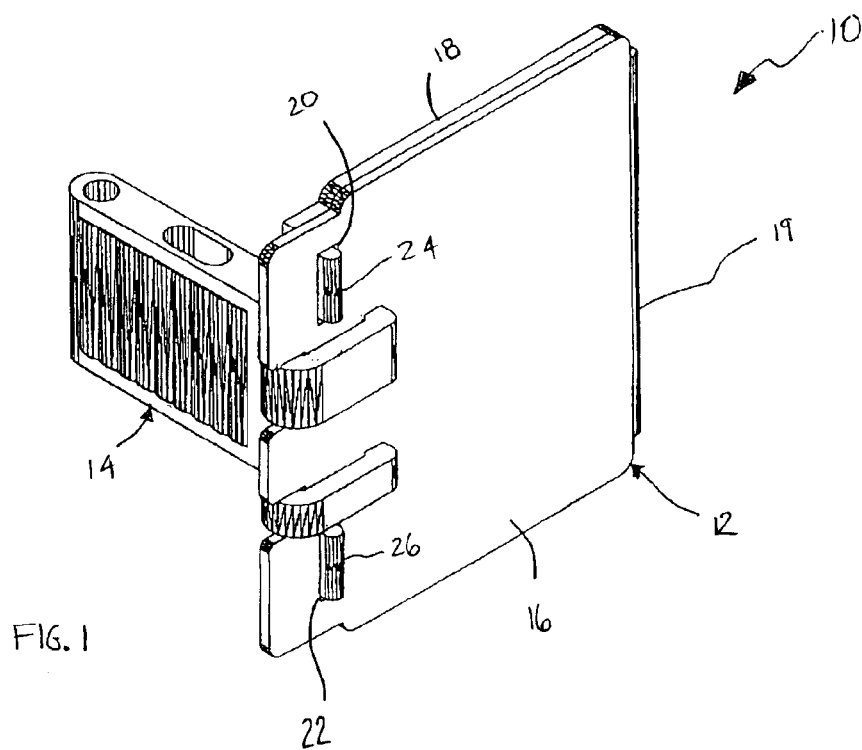
FIG. 1 is a first perspective view of a phosphor plate positioning device.
Figure 2:
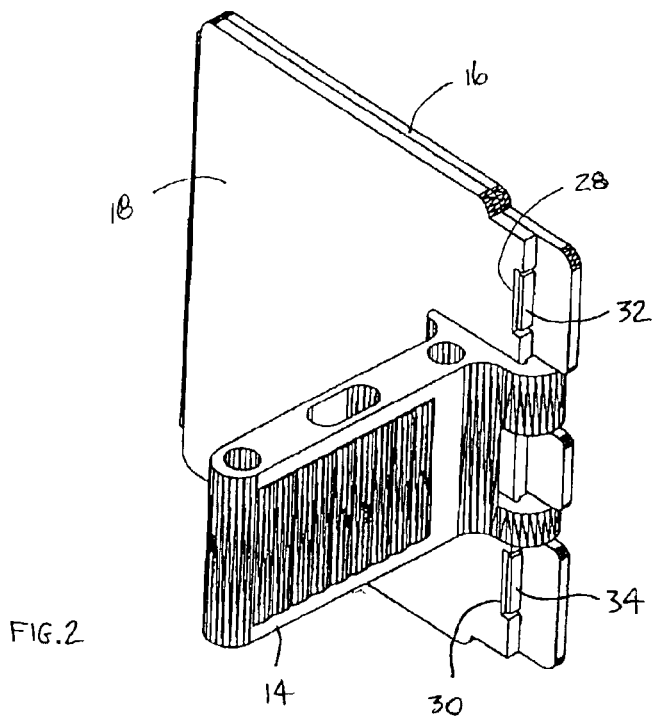
FIG. 2 is a second perspective view of a phosphor plate positioning device.

Referring initially to FIGS. 1 and 2, a preferred embodiment of a phosphor plate positioning device is shown and generally designated 10. FIGS. 1 and 2 show that, in general, the preferred phosphor plate positioning device 10 includes a phosphor plate magazine 12 and a support arm 14 for engaging and supporting the phosphor plate magazine 12. As shown, the phosphor plate magazine 12 includes a back plate 16 and a door 18 that is attached to the back plate 16 by a hinge 19. It can be appreciated that the door 18 can be attached to the back plate 16 by other means well known in the art.

FIGS. 1 and 2 show that the back plate 16 is formed with a generally rectangular upper opening 20 and a generally rectangular lower opening 22. The upper and lower openings 20, 22 are sized and shaped to receive an upper protrusion 24 and a lower protrusion 26, respectively, that extend perpendicularly from the door 18. Also, the door 18 is formed with an upper notch 28 and a lower notch 30. The back plate 16 includes an upper clip 32 and a lower clip 34 that engage the upper notch 28 and lower notch 30, respectively when the door 18 is rotated about the hinge 19 until the protrusions 24, 26 extend through the upper and lower openings 20, 22.

Figure 3:
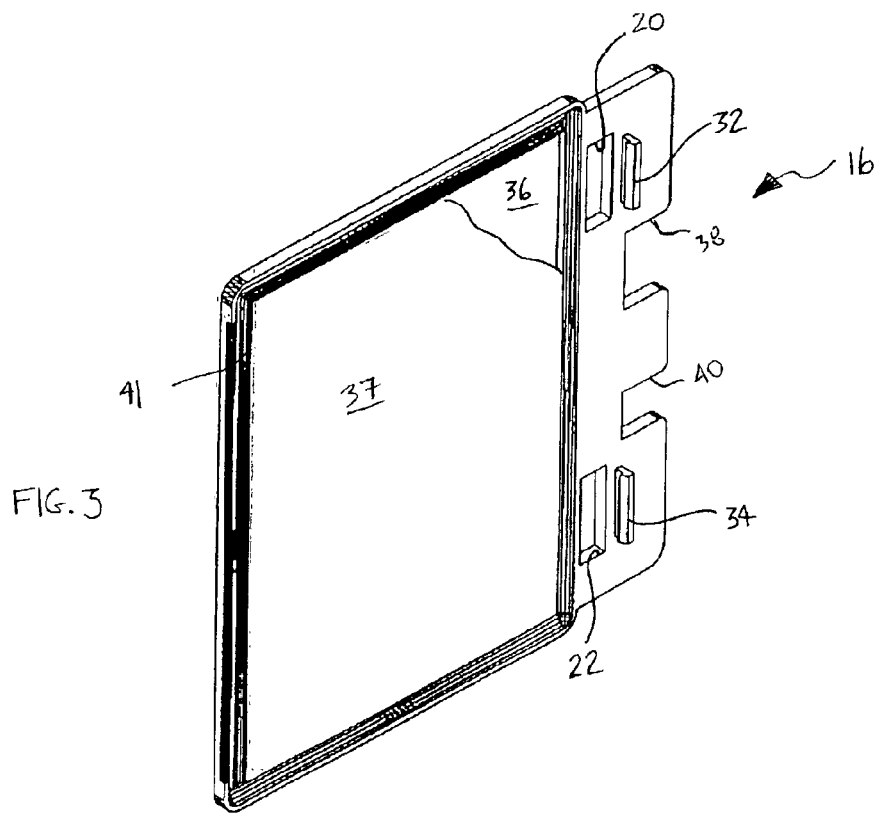
FIG. 3 is a perspective view of a back plate of the positioning device with the door and support arm removed for clarity.

Referring now to FIG. 3, it can be seen that the back plate 16 is preferably formed with an interior cavity 36. In a preferred embodiment, the interior cavity 36 is sized and shaped to receive a phosphor plate 37. It is to be understood that the dimensions of the interior cavity 36 can be sized so that the phosphor plate 37 fits snugly within the back plate 16. Also, it is to be understood that the back plate 16 and the door 14 are sufficiently rigid in order to protect the phosphor plate 37 from damage cause by bending or creasing. Moreover, it is to be understood that the back plate 16 can include a little flexibility that will allow a user, e.g., a dentist, dental assistant, etc., to push the back of the back plate 16 and effectively "pop" the phosphor plate 37 from the interior cavity 36 after it has been exposed to x-rays. Accordingly, the magazine 12 is non-flaccid, but bendable by a person in order to "pop out" a plate 37. FIG. 3 also shows that the back plate 16 forms an upper notch 38 and a lower notch 40 that are sized and shaped to receive respective fingers, described below, that extend from the support arm 14. FIG. 3 also shows that the back plate 16 includes a seal 41 that effectively seals the phosphor plate magazine when the door 18 is closed.

Figure 4:
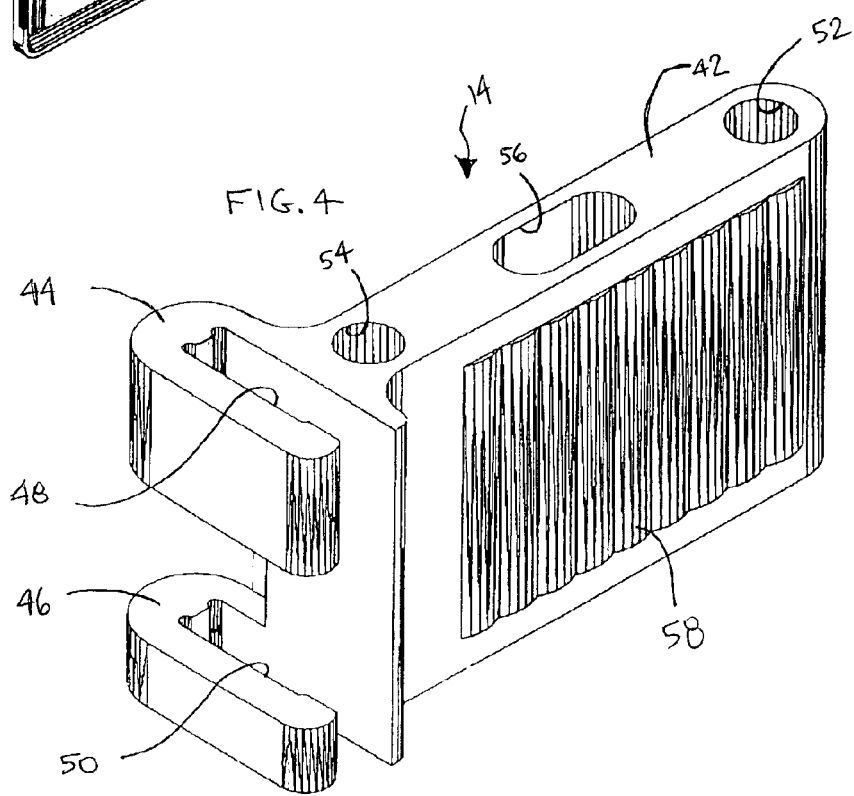
FIG. 4 is a perspective view of a support arm.

FIG. 4 shows details regarding the construction of the support arm 14. As shown, the support arm 14 includes an elongated base 42. An upper curved finger 44 and a lower curved finger 46 extend from the base 42. The fingers 44, 46 are bent in a "U" shape such that an upper slot 48 is formed by the upper finger 44 and a lower slot 50 is formed by the lower finger 46. When the support arm 14 engages the phosphor plate magazine 12, each finger 44, 46 fits into its respective notch 38, 40 formed by the back plate 16. The phosphor plate magazine 12 slides into the slots 48, 50 formed by the fingers 44, 46 and accordingly, the phosphor plate magazine 12 is held by the support arm 14 and the door 18 is further prevent from opening and exposing the phosphor plate 37 placed within the phosphor plate magazine 12.

As shown in FIG. 4, the elongated base 42 of the support arm 14 is formed with a first cylindrical bore 52 and a second cylindrical bore 54 distanced therefrom. An elongated elliptical bore 56 is formed between the first and second cylindrical bores 52, 54. It is to be understood that the bores 52, 54, 56 can be sized, shaped, and spaced such that the phosphor plate positioning device can be installed on an intraoral film positioner, e.g., the RAPD intraoral film positioner made by Flow X-Ray. Accordingly, the magazine 12 and phosphor plate 37 placed therein can be placed within a patient's mouth such that the phosphor plate 37 is parallel to the patient's teeth and the end of an x-ray cone of a dental x-ray machine.

FIG. 4 further shows that the support arm 14 also includes a knurled portion 58 along both sides of the elongated base 42. The knurled portion 58 of the support arm 14 provides a gripping surface and reduces the likelihood of a dental professional dropping the phosphor plate positioning device 10 when handling it.

Referring now to FIG. 5, an alternative embodiment of a phosphor plate positioning device is shown and generally designated 100. In general, this embodiment of the phosphor plate positioning device 100 includes a phosphor plate magazine 102 and a support arm 104. As shown, the phosphor plate magazine 102 includes a back plate 106 and a door 108 that is attached to the back plate 106 by a hinge 110. In this embodiment of the phosphor plate positioning device 100, the support arm 104 is integrally formed with the back plate 106.

FIGS. 6 and 7 show that the back plate 106 is formed with an interior cavity 112. Preferably, the interior cavity 112 is sized and shaped to snugly receive a phosphor plate 113. As shown in FIGS. 6 and 7, the back plate 106 is formed with a rib 114 adjacent to the cavity 112. The door 108 is formed with a corresponding groove 116. In this embodiment, the door can be rotated about the hinge 110 toward the back plate 106, until the groove 116 snaps over the rib 114 and engages the rib 114. Accordingly, when the groove 116 is snapped over the rib 114, the door 108 can not easily rotate away from the back plate 106 and expose a phosphor plate 113 placed inside. FIGS. 6 and 7 show that the back plate 106 also includes a seal 118 around the cavity that seals the cavity 112 within the phosphor plate magazine 102 when the door 108 is closed and the groove 116 engages the rib 114.

It is to be understood that either embodiment of the phosphor plate positioning device 10, 100 is preferably made from a durable plastic or resin that can withstand the autoclaving that is commonly used in the dental industry. Further, either embodiment of the phosphor plate positioning device 10, 100 can preferably withstand a minimum of one hundred autoclave cycles and remain useful.

With the configuration of structure described above, the phosphor plate positioning device 10, 100 can be used to protect the phosphor plate from damage caused by moisture, bending, or other mishandling. Thus, the useful lives of phosphor plates used in conjunction with the phosphor plate positioning device 10, 100 can be maximized.

While the particular PHOSPHOR PLATE POSITIONING DEVICE as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

I claim:

1. A phosphor plate positioning device, comprising:
   a rigid magazine including a door defining a continuous windowless surface and a back plate defining a continuous windowless surface, whereby light cannot enter the magazine when the windowless surfaces are juxtaposed with each other;
   a cavity formed within the magazine, the cavity being sized and shaped to receive a phosphor plate; and
   a rigid support supporting the magazine and configured for engagement with an intraoral film positioner.

2. The device of claim 1, wherein the back plate forms the cavity and is hinged to the door.

3. The device of claim 1, wherein the support arm is integrally formed with the back plate.

4. The device of claim 3, further comprising:
a seal circumscribing the cavity.

5. The device of claim 4, wherein the support arm is formed with at least one bore.

6. The device of claim 5, wherein a portion of the support arm is knurled.

7. The device of claim 6, wherein the back plate comprises:
a rib adjacent to the cavity.

8. The device of claim 7, wherein the door comprises:
a groove configured to engage the rib in order to keep the door closed.

9. An in-mouth system for dental imaging consisting essentially of:
at least one phosphor plate; and
a non-flaccid magazine sized to hold the plate, the magazine being at least partially opaque to prevent at least one surface of the phosphor plate from being exposed to light when the plate is held in the magazine.

10. The system of claim 9, wherein the magazine forms a cavity that is sized and shaped to receive the phosphor plate.

11. The system of claim 10, wherein the magazine comprises:
a back plate forming the cavity; and
a door hingedly attached to the back plate.

12. The system of claim 11, wherein the system is configured for engaging a support arm.

13. The system of claim 12, wherein the support arm is integrally formed with the back plate.

14. The system of claim 13, further comprising:
a seal circumscribing the cavity.

15. The system of claim 14, wherein the support arm is formed with at least one bore.

16. The system of claim 15, wherein a portion of the support arm is knurled.

17. The system of claim 16, wherein the back plate comprises:
a rib adjacent to the cavity.

18. The system of claim 17, wherein the door comprises:
a groove configured to engage the rib in order to keep the door closed.

* * * * *